United States Patent [19]

Langley et al.

[11] Patent Number: 5,035,900

[45] Date of Patent: Jul. 30, 1991

[54] METHODS OF DRYING BIOLOGICAL PRODUCTS

[75] Inventors: John Langley, Shipley; Kenneth C. Symes, Keighley, both of Great Britain; Peter Holm, Stenlose, Denmark

[73] Assignee: Allied Colloids Ltd., England

[21] Appl. No.: 398,057

[22] Filed: Aug. 24, 1989

[30] Foreign Application Priority Data

Aug. 24, 1988 [GB] United Kingdom ............... 8820061
Aug. 24, 1988 [GB] United Kingdom ............... 8820062
Jan. 19, 1989 [GB] United Kingdom ............... 8901183
Jan. 19, 1989 [GB] United Kingdom ............... 8901193

[51] Int. Cl.$^5$ .................. A61K 9/14; A61K 9/50; A61K 31/695
[52] U.S. Cl. ................... 424/484; 424/486; 424/487; 424/488; 424/499; 424/81; 514/57; 514/938; 536/56; 536/63
[58] Field of Search ............ 424/484, 486, 487, 499, 424/488, 81; 514/57, 938; 536/56, 63

[56] References Cited

FOREIGN PATENT DOCUMENTS

| 0128661 | 5/1984 | European Pat. Off. . |
| 61254244 | 11/1986 | Japan . |
| 63105098 | 5/1988 | Japan . |
| 1353317 | 5/1974 | United Kingdom . |

Primary Examiner—Thurman Page
Assistant Examiner—G. S. Kishori
Attorney, Agent, or Firm—Ostrolenk, Faber, Gerb & Soffen

[57] ABSTRACT

Enzymes and other biologically produced materials are recovered from the fermentation broth or other liquor in which they are provided initially and simultaneously distributed throughout particles of a polymeric matrix by dissolving the polymer in the liquor, dispersing the resultant polymer solution in a non-aqueous liquor in the presence of a stabiliser, and azeotroping the dispersion to produce either dry beads or a dispersion of small particles in the non-aqueous liquid.

12 Claims, No Drawings

METHODS OF DRYING BIOLOGICAL PRODUCTS

Biologically produced materials are generally provided initially in the form of a dilute aqueous liquor. For instance natural products may be extracted from plants by squeezing or solvent extraction to form an aqueous liquor containing the natural product and fermentation products are made by fermentation in a fermentation broth. Examples are macromolecular materials such as xanthan and other microbial polysaccharides, enzymes, spores, mycelia, bacteria and cellular materials.

The fermentation broth can be concentrated to a fermentation broth concentrate by conventional techniques comprising filtration (for instance centrifuging) and/or ultra filtration, and these can be facilitated by, for instance, flocculation. However the concentrate still contains a relatively large amount of water. It is therefore necessary to evaporate this. Similarly it is necessary to evaporate the plant extracts.

Many biologically produced material are liable to be damaged by exposure to heat and so it is necessary to try to avoid overheating, even on a microscopic scale, during the drying.

It is often desirable, or in some instances necessary, to provide the dried biologically produced material in the form of particles containing that material encapsulated by polymeric material, either as a shell around the biological material or as a matrix through which the biological material is distributed. For instance, one method of drying a fermentation liquor that is widely used involves spray drying, but a difficulty with spray drying is that it generates a large amount of dust, and dusting of the product can create serious problems. The process must therefore be conducted under carefully controlled conditions-and it is generally necessary to agglomerate the product, for instance by spray drying it with a binder or by applying a binder to the dried product. However dusting remains a problem and spray drying can damage the fermentation product. For instance there can be a significant loss in enzymatic activity during spray drying a broth or concentrate containing enzymes.

Attempts have been made to combine encapsulation with drying of an enzyme solution. Thus, in JP 75-22506 polysaccharide or polyacrylamide polymer is added to an enzyme solution before spray drying, in DE 2,435,008 a solution of methyl cellulose is sprayed on to a fluidised bed of an enzyme and in GB 1,377,725 aqueous enzyme solution is sprayed on to a fluidised bed of starch but these methods still tend to give dusting problems and can give non-uniform coating with the polymer.

In EP 0128661 and 0180366 there are described methods of drying polysaccharides comprising emulsifying a fermentation concentrate into a water immiscible liquid and then either azeotroping it to form a concentrated dispersion or spray drying it. However these methods do not provide the required polymeric matrix.

A method of providing this is described in EP 0284367 but it requires formation of the polymeric matrix by polymerisation from monomer in the presence of the microbial polysaccharide and this incurs certain disadvantages. Thus other processes are known in which the biological material is incorporated into a monomer mixture that is polymerised to form the polymeric matrix. For instance, in Chemical Abstracts Vol 85 147053J an enzyme is encapsulated in particles of a cross linked acrylamide acrylic acid copolymer as a result of being blended with the monomers prior to suspension polymerisation. However some biological materials inhibit the polymerisation. Others are desensitised by contact with monomeric or other components present during the polymerisation process. In particular, the polymerisation is generally exothermic and many active ingredients are sensitive to the high temperatures generated within the polymeric matrix during the polymerisation. For example the active ingredient may be deactivated or may be volatilised out of the polymerisation mixture. For instance it is generally necessary to avoid exposing enzymes to the temperatures that prevail during conventional bead polymerisation or other exothermic polymerisation processes.

Methods have been proposed for trying to minimise the problems caused by the exothermic polymerisation (see for instance EP 239633 and Chemical Abstracts volume 95 81582c). However all these methods incur serious practical disadvantages. It is also known to use a polymerisation mixture comprising a blend of monomer and a difunctional low molecular weight polymer as cross linking agent (U.S. Pat. No. 4,177,056) but this process still involves exposing the active ingredient to the monomer and the exotherm.

In W083/03102 the active ingredient is either mixed with monomers which are then polymerised (thus incurring the disadvantages discussed above) or is mixed into a solution of a pre-formed polymer which is dispersed in a non-aqueous medium and is gelled in that medium, for instance by cooling, cross linking, neutralisation followed by heating or enzymatic reaction. These processes are all rather difficult to operate successfully and, in particular, it is difficult to obtain particles having adequate physical strength. This method may be suitable for making laboratory reagents but is inapplicable to large scale commercial production.

In JP-A-61-254244 enzyme and water soluble polymer are dispersed in liquid hydrocarbon and then acetone is added. Although the use of a "culture solution" is mentioned, it is clear that the intention is to precipitate the polymer around the enzyme, rather than to form a matrix throughout which the enzyme is distributed, and for this purpose a previously dried enzyme can be used. If the resultant "shell" of polymer is damaged, all the "core" of enzyme is exposed to the environment. We aim at distributing the enzyme throughout a polymeric matrix so as to avoid this risk.

In JP-A-63-105098 relatively large (e.g., 150 to 800μm) microcapsules are made that are suitable for use in liquid or gel detergents and one method of manufacture that is mentioned, but not exemplified, involves dispersing into a hydrophobic solvent an aqueous phase containing enzyme, polyhydroxy compound and polyvinyl alcohol and then removing the water content by heating or reducing pressure.

In GB 1,353,317, various methods are described for forming a precipitated complex between an enzyme and an anionic polymer, and in example 2 this is achieved by adding a particular polymer solution to a concentrated culture filtrate followed by the addition of acid to form a precipitate which is then filtered and washed with acetone.

If a method of recovering dry biological material, distributed throughout a polymeric matrix, is to be commercially successful, it must be operable reproducibly on a large commercial scale, but none of the techniques described in the literature offer this possibility.

In the invention, particles containing biologically produced material distributed through a matrix of polymeric material are made by mixing polymeric material with an aqueous liquor that contains the biologically produced material and that is a fermentation liquor or a plant extract to form an aqueous polymer phase containing the biologically produced material substantially uniformly distributed throughout the phase, simultaneously or subsequently dispersing the aqueous phase as a water immiscible liquid in the presence of a dispersion stabiliser to form a substantially stable dispersion, and azeotroping the dispersion to form substantially dry particles each comprising a matrix of the polymeric material with the biologically produced material dispersed substantially uniformly throughout the matrix.

The process of the invention has the great advantage that it produces the desired polymeric particles in a single stage starting from an aqueous fermentation liquor or aqueous plant extract in which the biological material is first produced. Thus in the invention it is not necessary to extract the biological material from its initial liquor, e.g., by spray drying, before combining it with the polymer and, instead, the process of the invention is used as a simultaneous recovery and encapsulation process. Thus the process avoids, for instance, the difficulties of spray drying followed by agglomeration or encapsulation.

It avoids the exposure of the fermentation product to the exotherm, initiator and other conditions associated with a polymerising mixture. It allows the drying to be carried out under carefully controlled conditions so as to avoid overheating both on a macro scale and on a micro scale. Since the heating can be controlled very carefully, it is possible to minimise the risk of deactivation of the biological material and thus it is possible to produce particles having a very satisfactory biological activity, often considerably greater than can conveniently be made by known recovery techniques.

The size of the substantially dry particles is dictated by the size of the dispersed aqueous phase particles in the immiscible liquid. It is often desired that the dry particles are beads that have a size of at least 30μm, often at least 100 μm, for instance up to 500μm or up to lmm or even 2mm or larger. With particles of this size, the substantially dry particles will be separated from the water immiscible liquid by filtration, centrifugation or other conventional separation methods and may be subjected to further drying after the separation. This further drying may be by solvent exchange but is preferably by warm air, for instance in a fluidised bed.

The beads must be dried sufficiently that they are non-sticky and are generally dried to a moisture content that is in equilibrium with the environment or is drier than this.

A particular advantage of the invention is that it is easily possible to produce beads of a very regular shape and narrow size range. This is only possible because the drying is by azeotroping and because the active ingredient and polymer are first dispersed in water-immiscible liquid.

Although the production of these beads is usually preferred, another benefit of the process is that it is possible also to make much smaller, dry, particles. Thus the particles may, however, be below 30μm, for instance generally below 10μm and often below 3μm. If such particles are separated from the water immiscible liquid there is a risk of dusting problems and such particles are preferably left as a stable dispersion in the immiscible liquid. These do not have to be dried to atmospheric equilibrium and may be left with, for instance, a moisture content of 25% based on the polymer. Preferably however they are dried to atmospheric equilibrium or less, e.g., below 10% moisture based on polymer.

An important feature is that the biological material is not protected from the environment merely by an encapsulating shell of polymer (that is liable to become damaged) but is instead protected by being distributed throughout a matrix of the polymer. Sufficient polymer must be present to form a continuous matrix and to give the particles the strength, release or other properties that are required. Generally this means that the amount of polymer must be at least 0.5 times the amount of active ingredient (on a dry weight basis). Preferably there is an excess of polymer, for instance at least two times the amount of active ingredient and preferably there is a large excess, for instance at least seven times. The use of this seven-fold excess (or more) of polymer means that the biological material is protected very effectively from the environment and even if the particles are damaged the amount of active ingredient that is liable to be exposed to, or escape into, the environment is very low. Generally the amount of polymer is at least 10 times and usually at least 15 times the amount of active ingredient (on a dry weight basis). It is usually unnecessary for it to be more than 50 times, and amounts in the range 15 to 30 times are often suitable although amounts up to 100 times or more can be used.

Small amounts of filler and other additives can be included in the matrix. Generally the polymeric material constitutes at least 50%, preferably at least 75% and most preferably at least 90% by weight of the solid composition formed of a matrix, active ingredient and any inert material distributed through the matrix.

The biologically produced material that is encapsulated by the process of the invention can be a plant extract, for instance a natural oil or other essence or flavour that is squeezed from or extracted from the whole or part of a plant, or it can be a fermentation product such as enzymes, fungi, spores, bacteria or cells, or secondary metabolites from them such as antiobiotics. When it is a plant extract, the aqueous medium is usually a dilute aqueous solution of the natural oil or other essence. When, as is preferred, it is a fermentation product this is provided initially as a fermentation liquor which can be the fermentation broth itself or may be a filtrate or concentrate derived from the broth. For instance when the biologically produced material is a soluble component, for instance an enzyme, the broth will often first have been filtered to remove insoluble cellular material. Concentration techniques that can be carried out on the broth, or a filtrate of the broth, before use in the invention include standard concentration techniques such as flocculation and/ultra filtration.

The invention is of particular value when the active ingredient is one that would interfere with or be damaged by monomer from which the polymer is made or would tend to be deactivated (either by evaporation or desensitisation) if exposed to exothermic polymerisation. The invention is therefore of particular value when the active ingredient is a sensitive material that is liable to be desensitised.

One particularly preferred type of active ingredient is an enzyme. The enzyme is preferably a protease, especially an alkaline protease, of the type used in washing powders or other detergents, but other suitable enzymes for these purposes include amylases and lipases.

Naturally if the enzyme is to be included in a solid detergent, then the particles of the invention will preferably be in bead form. If it is to be included in a liquid detergent then it is generally preferred for the product to be in the form of a dispersion of the particles in non-aqueous liquid.

Another preferred type of active ingredient is a microbial agriculturally or pharmaceutically useful product such as an antibiotic for human and/or veterinary use, a biopesticide, bioherbicide or biofertiliser. An example is Bacillus Thuringiensis toxin for killing lavae. With this, and with many other microbial products, the cells can be encapsulated either dead or alive because it is the toxic protein within the cell, rather than the living cell that is required. However in some instances it is desirable for the cell to be alive within the polymeric matrix in order that it can metabolise and multiply as soon as it is released from the matrix, for instance on a leaf surface, in the ground, or at some point in the alimentary canal.

Other suitable biological materials are bacteria, or enzymes derived from bacteria, suitable for use in silage or compost manufacture for promoting the necessary silaging or composting fermentation processes. Other suitable biological materials are enzymes or whole cells that can be used for breaking down fats, cellulose or proteins, or for removing nitrates or heavy metals, from effluent streams or from water that is being purified for use as, for instance, potable water.

The polymer should be film forming in the sense that the polymeric residue will form a coherent matrix as a result of the azeotropic evaporation of most or all of the water.

The polymer is preferably soluble in the aqueous liquor containing the biologically produced material and may be introduced into the aqueous liquor either as a preformed aqueous solution or in any other convenient form. The polymer can be a natural or modified polymer such as a starch or a cellulose (e.g., carboxy methyl cellulose) or gum. Preferably it is a synthetic polymer formed from an ethylenically unsaturated water soluble monomer or monomer blend, which may be non-ionic or ionic.

Suitable anionic monomers are ethylenically unsaturated carboxylic or sulphonic monomers, most preferably monomers such as (meth) acrylic acid, crotonic acid, itaconic acid, maleic acid, (meth) allyl sulphonic acid, vinyl sulphonic acid and 2-acrylamido-2-methyl propane sulphonic acid. Acrylic or methacrylic acid is preferred.

Suitable cationic monomers are dialkylaminoalkyl (meth)-acrylamides and, preferably, -acrylates, usually as acid addition or quaternary ammonium salts. Particularly preferred are monomers such as diethylaminoethyl (meth) acrylate.

Suitable non-ionic monomers of this type are (meth) acrylamide and hydroxy-lower alkyl (meth) acrylates. The anionic and cationic monomers may be either in the free acid or free base form when they are sufficiently soluble in this form (for instance acrylic acid) but more usually in the form of an alkali metal or ammonium salt of anionic monomers or an acid addition or quaternary ammonium salt of cationic monomers.

The preferred polymer is usually based on 0-50% acrylamide and 50-100% acrylic acid or soluble salt thereof.

The soluble polymer may have been made by any conventional polymerisation technique, such as reverse phase suspension polymerisation, solution polymerisation, reverse phase bead polymerisation or gel polymerisation. Alternatively, the polymer may be a copolymer of soluble and insoluble monomers (e.g., methacrylic acid and ethyl acrylate) and may have been made by oil-in-water emulsion polymerisation followed by addition of sodium hydroxide or other alkali to convert it to a soluble form.

Instead of introducing the polymer in a soluble form, the polymer can be a polymer that is insoluble in water but is soluble in alkali and which is introduced as an oil-in-water emulsion that has been made by emulsion polymerisation of ethylenically unsaturated monomer or monomer blend that is insoluble in the water phase of the polymerisation mixture. The monomers are generally a blend of anionic solubilising monomers (typically selected from the anionic monomers discussed above) and ethylenically unsaturated non-ionic monomers, the overall blend being insoluble at the pH of the emulsion. Thus the emulsion polymerisation may be conducted at a pH below 7 but when the polymer is subsequently exposed to more alkaline conditions the polymer becomes soluble (or highly swellable). Suitable non-ionic water insoluble monomers include alkyl (meth) acrylates, styrene, acrylonitrile, vinyl chloride, vinyl acetate or vinyl butyl ether. Ethyl acrylate is preferred, with the polymer preferably being formed from 10 to 70% methacrylic acid or other anionic monomer, 10 to 70% ethyl acrylate or other insoluble monomer and 0 to 70% acrylamide or other soluble non-ionic monomer.

The use of an emulsion polymer of this type is of particular value when it is desired for the polymeric matrix to permit substantially no release of the biological material in one environment (for instance neutral or acidic) and rapid release in an alkaline environment.

Controlled release of biological material can also be obtained when the polymer is introduced initially as a salt with a volatile amine (for instance ammonia) of a polymer derived from ethylenically unsaturated carboxylic acid monomer such as (meth) acrylic acid. The salt is soluble in water but the ammonia or other volatile amine evaporates during the azeotroping to render the polymer less hydrophilic. Accordingly at least the outer shell of the particles, and possibly substantially the entire polymeric matrix, will be less hydrophilic and water soluble than when the carboxylic groups are in alkali or amine salt form. The particle therefore has relatively low permeability to ambient moisture but, uon exposure to a slightly alkaline aqueous solution (for instance as typically prevails in a wash liquid) the polymer will be sufficiently solubilised to permit rapid release of the trapped enzyme or other biological material. For this purpose the polymer is preferably based on 0 to 50% acrylamide and 50 to 100% acrylic acid or, preferably, methacrylic acid. Products of these types are described in more detail in our copending application No. 07/398,088 filed even date herewith.

The molecular weight of the polymer will be selected having regard to the concentration and solution viscosities that are required and, especially, the gel strength that is required in the final beads. If the molecular weight of a solution polymer is too high it can be difficult to form a stable dispersion of aqueous polymer particles containing a commercially useful concentration of active ingredient and so for many polymers the molecular weight should be below 1 million, often below 500,000. If the molecular weight is too low the final gel strength may be inadequate, even if the beads do have surface cross linking. In some instances the molecular weight may be down to, for instance, 4,000 or even 2,000. A range of 5,000 to 300,000 is often suitable.

The polymers that are used in the invention may be unreactive polymers, i.e., polymers that cannot undergo any significant chain extension even though it may be possible to cause cross linking through pendant groups since any such cross linking does not usually result in any significant exotherm or other conditions that might damage the active ingredient. It is also possible to use a polymer that undergoes chain extension by addition polymerisation during the process provided this does not involve the presence of deleterious amounts of initiator, exotherm or other conditions that might damage the active ingredient. The risk of this can be minimised by ensuring that the reactive polymer already has a substantial chain length, for instance at least 50 and usually at least 100 carbon atoms in the chain. Depending upon the degree of unsubstitution in the reactive polymer, the final polymer may be linear or may be cross linked and, if cross linked, the polymeric matrix will then be swellable rather than soluble. Preferred reactive polymers are described in EP-A-0328321.

The polymer may undergo cross linking before, after or preferably during the azeotroping. For instance it is known that many polymers, especially those containing anionic groups, can undergo ionic cross linking if exposed to polyvalent metal compounds and so the inclusion of such compounds in the aqueous solution of polymer or in the non-aqueous liquid or both can result in cross linking. If the polyvalent metal compound is preferentially soluble in the non-aqueous liquid (for instance being aluminium isopropoxide or other polyvalent metal alkoxide) then the cross linking will be concentrated primarily at the surface of the particles. If the cross linking agent is preferentially soluble in the aqueous solution of polymer then the cross linking may occur substantially uniformly throughout the particles. Cross linking agents such as glutaraldehyde can be used with appropriate polymers.

By appropriate selection of the type and amount of cross linking it is possible to control the physical properties of the particles. For instance it is possible to control the release of active ingredient from the particles and/or to increase the gel strength of the particles and/or to increase the hardness, or reduce the stickiness, of the surface of the particles. Also, if the cross linking is concentrated on the surface of the particles, the resultant particles tend to dissolve more rapidly into water.

Instead of achieving cross linking during the process of the invention, it is also possible (especially when the polymer is initially produced as an oil-in-water emulsion) to provide the polymer initially as a cross linked polymer. However generally the polymer is linear and has been made substantially in the absence of cross linking monomer or other cross linking agent.

The polymer can serve to give controlled release, for instance under selected pH conditions as described above, or can serve merely as a relatively inert material that will bond the biological material into the desired on-dusty particles and that will give release at the appropriate time, or the polymer can serve to provide useful properties in the environment in which the biologically active material is to be used. In particular, when the biological material is an enzyme that is to be included in a detergent it is particularly convenient for the polymeric matrix to be a polymer that is useful as a component in a detergent, for instance as a detergent builder or detergent anti-redeposition aid. Suitable polymers include carboxy methyl cellulose polyvinyl pyrollidone, polyvinyl alcohol and anionic synthetic polymers, for instance polymers of ethylene and (meth) acrylic acid and other polymers preferably of molecular weight 4,000 to 300,000 and formed from water soluble ethylenically unsaturated carboxylic or sulphonic monomer, optionally with water soluble non-ionic monomer. Preferably the polymer is of sodium polyacrylate but copolymers with arylamide and homopolymers or copolymers with, for instance, allyl sulphonate or 2-acrylamido methyl propane sulphonate may be used. Copolymers of maleic anhydride with, for instance, acrylic acid are also suitable.

The polymeric material can be blended with the fermentation liquor or other aqueous liquor containing biological material to form an aqueous polymer phase containing both the polymer and the biological material, and this phase can then be dispersed in the water immiscible liquid. Alternatively, the fermentation liquor or plant extract can be dispersed in the water immiscible liquid and the polymer then added (usually as a preformed solution or emulsion) or alternatively the polymer can be dispersed and the fermentation broth or plant extract then added. In each instance sufficient agitation should be provided to ensure that the dispersed aqueous particles in the water immiscible liquid have a substantially uniform content of both polymer and biological material.

The aqueous phase must itself be substantially stable since if there is a tendency for it to undergo phase separation this will interfere with the formation and maintenance of a uniform dispersion in the water immiscible liquid. The aqueous phase is preferably therefore one which is stable in bulk and does not undergo phase separation. If the active ingredient is ionic, it is preferred for the polymer to be non-ionic or co-ionic. For instance when the active ingredient is an enzyme, which is slightly cationic, there can be a risk that some anionic polymers may cause destabilisation, in which event the aqueous phase should be sEabilised. This can be achieved by thickening the aqueous phase and/or by adding a polyhydroxy compound, especially sucrose or other sugar or a glycol or other low molecular weight polyhydroxy compound, e.g., propylene glycol.

The aqueous phase can also include other additives that are optional for the intended use of the final product. For instance the solution may often contain inert fillers such as clays and/or pigments or dyes.

The resultant dispersion of aqueous particles containing polymer and active ingredient must be sufficiently stable that it can be subjected to azeotropic distillation and for this purpose it is generally necessary for the dispersion to include a polymeric dispersion stabiliser, at sometimes also an emulsifier surfactant.

The concentration of the polymer in the polymer solution will be selected according to the molecular weight and solution viscosity of thepolymer but is often in the range 5 to 50%, typically 20 to 30%.

The particle size of the aqueous droplets and the final dry particles can be controlled by choice of the amount of shear to which the dispersion is subjected, choice and amount of stabiliser, and choice and amount of surfactant. When the end product is to be a stable dispersion in oil or other immissible liquid, it is preferred to use a water-in-oil emulsifier to promote the formation of small particles having a size below 10μm, for instance below 3μm. However when beads are required, for instance above 30 and usually above 70μm, the emulsifier may be omitted.

The polymeric stabiliser is generally an amphipathic stabiliser, for instance, formed from hydrophilic and hydrophobic acrylic monomers. Suitable surfactants, non-aqueous liquids and polymeric stabilisers, and suitable azeotroping conditions, are described in, for instance, EP 0128661 and EP 0126528. The stabilisers described in GB 2,002,400 or, preferably, 2,001,083 or 1,482,515 are particularly preferred.

The immiscible liquid is non-aqueous and must include liquid that will form an azeotrope with water. Often the water immiscible liquid is a blend of a relatively high boiling liquid that remains in the dispersion and a low boiling liquid that is azeotroped from the dispersion. The temperature at which azeotroping occurs is generally below 100° C. and is controlled by the choice of liquid and, especially, the pressure at which the distillation is conducted. Generally the distillation is conducted under reduced pressure and when the active ingredient is temperature sensitive (e.g., an enzyme) the reduced pressure is preferably such that the azeotroping occurs at a maximum temperature of not more than 80° C., often below 70° C. and most preferably below 50° C. For instance by applying a relatively high vacuum it is possible to azeotrope at very low temperatures, for instance as low as 30° C. Sodium sulphate or other salt may be added to lower the azeotroping temperature.

The polymer should be film forming at the distillation temperature, and usually is film forming at 20° C. or lower.

After azeotroping sufficient of the water from the particles to convert the particles into a substantially solid and non-sticky form, the particles (if sufficiently large) can then be separated from the non-aqueous liquid and can be further dried, if desired, in conventional manner, for instance on a fluidised bed.

Before or after azeotroping, the particles may be given a surface treatment to adjust their properties. For instance a polymer containing a water soluble salt of a relatively insoluble monomer may be converted to its less soluble form (e.g., sodium methacrylate in the surface of the particles may be converted to methacrylic acid). A relatively insoluble polymer or other hydrophobic material may be applied (e.g., an oil-in-water emulsion polymer may be applied, and will dissolve when the particles are mixed with wash water).

The following are some examples.

EXAMPLE 1

A 25% aqueous solution is formed of sodium polyacrylate having molecular weight 30,000 and is blended with sufficient of fermentation broth containing a detergent alkaline protease (or an amylase or lipase) to give a polymer:enzyme dry weight ratio of 9:1. The solution is stirred into a paraffinic oil in the presence of an amphipathic polymeric stabiliser formed from stearyl methacrylate, methyl methacrylate and methacrylic acid. The resultant dispersion is subjected to azeotropic distillation under reduced pressure such that the maximum temperature in the dispersion does not exceed about 50° C. Once sufficient water has been taken off for the dispersed particles to be substantially dry to touch, they are separated from the remaining liquid by filtration and can then be further dried in conventional manner. They have a particle size in the range 100 to 100μm.

The resultant beads are non-dusting and so can be handled with safety. When a detergent powder containing them is mixed with water, they rapidly dissolve to release the enzyme into the water.

EXAMPLE 2

A solution is formed of 640 g 25% sodium polyacrylate and 160 g of a fermentation broth concentrate that is a 5% detergent protease solution (i.e., 8 g dry weight enzyme and 160 g dry weight polymer) and its pH is adjusted to 7. 1600 g of a water immiscible, aliphatic hydrocarbon liquid (Solvent 41) and 53 g of a 15% solution in organic solvent of an amphipathic polymeric stabiliser is charged to a 3 litre resin pot equipped with a mechanical stirrer and a Dean & Stark apparatus connected to a condenser and the aqueous phase is added and the mixture stirred for five minutes, leading to the formation of small bead droplets. The contents are then warmed to 45° C. and the pressure reduced sufficiently to cause solvent and water to distill azeotropically. The volume of water that is removed is observed and distillation is continued until no further water is collected (at least 2 hours).

The contents of the flask are cooled, the beads filtered, washed in acetone and dried in hot air.

The final product has 12 to 15% mOisture content, is in the form of beads of regular almost spherical shape that are hard and free flowing and dissolved readily in cold and hot water. The beads have a narrow size range of approximately 250 to 500μm and the product was substantially free of dust.

EXAMPLE 3

The process of example 2 is repeated except that 5% (on dry polymer and enzyme) of titanium dioxide is added to produce beads that are almost white and opaque.

EXAMPLE 4

The process of example 2 is repeated except that the aqueous phase is formed of 160 g dry weight sodium polyacrylate, 160 dry weight sucrose and water to make 800 g. The beads have an active protein content of about 3% and have similar properties to those described in example 2. White beads could be obtained by replacing 16 g sucrose by 16 g titanium dioxide.

EXAMPLE 5

The process of example 2 is repeated except that the sodium polyacrylate is replaced with the same weight of ammonium polymethacrylate. The matrix in the final beads is formed of a mixture of polymethacrylic acid and ammonium polymethacrylate, with the majority of the polymer in the outer shell being in the form of the free acid. The beads have less permeability to moisture than the beads of example 2 but dissolve rapidly when mixed into a weakly alkaline solution.

EXAMPLE 6

The process according to example 2 is repeated except that the 25% sodium polyacrylate solution is replaced by a 25% emulsion at pH 4 of a copolymer of methacrylic acid and butyl acrylate.

The beads are substantially insoluble and non-swelling in tap water but dissolve rapidly when exposed to an alkaline environment. By appropriate choice of the proportions of methacrylic acid and butyl acrylate it is possible to select the pH at which release occurs.

EXAMPLE 7

The process of example 2 is repeated except that a small amount of a water-in-oil emulsifier (5 g of sorbitan mono-oleate) is included in the aqueous phase and the dispersion is formed by the application of high shear. The azeotroped product is a stable dispersion in the water immiscible liquid of particles having a size below 3 μm.

We claim:

1. A process for making particles containing biologically produced material selected from the group consisting of enzymes, fungi, spores, bacteria, cells and antibiotics, in a matrix of polymeric material comprising:
    mixing film-forming polymeric material selected from the group consisting of water soluble polymers and oil-in-water emulsions of alkaline soluble polymers, the said polymeric material bring in an amount of at least 0.5 times that of the biologically produced material on dry weight basis, with an aqueous liquor that is a fermentation broth concentrate containing the said biologically produced material and thereby forming an aqueous polymer phase throughout which the biologically produced material is substantially uniformly distributed,
    simultaneously or subsequently dispersing the said aqueous polymer phase in a water immiscible liquid in the presence of a dispersion stabilizer and thereby forming a substantially stable dispersion of the said aqueous polymer phase in the said water immiscible liquid, and
    azeotropically distilling the dispersion at a temperature that is below 70° C. and at which deactivation of the biologically produced material does not occur, and thereby forming substantially dry particles each comprising a matrix formed of polymeric material and the biologically produced material dispersed substantially uniformly throughout the matrix, wherein the particles are beads having a size of from 30 μm to 2 mm or the particles have a size of below 10 μm and are present as a stable dispersion of the particles in the water immiscible liquid.

2. A process for making particles containing biologically produced material selected from the group consisting of enzymes, fungi, spores, bacteria, cells and antibiotics, in a matrix of polymeric material comprising:
    mixing film-forming polymeric material selected from the group consisting of water soluble polymers and oil-in-water emulsions of alkaline soluble polymers, the said polymeric material bring in an amount of at least 0.5 times that of the biologically produced material on dry weight basis, with an aqueous liquor that is a fermentation broth concentrate containing the said bilogical produced material and thereby forming an aqueous polymer phase throughout which the biologically produced material is substantially uniformly distributed,
    simultaneously or subsequently dispersing the said aqueous polymer phase in a water immiscible liquid in the presence of a dispersion stabilizer and thereby forming a substantially stable dispersion of the said aqueous polymer phase in the said water immiscible liquid,
    azeotropically distilling the dispersion at a temperature that is below 70° C. and at which deactivation of the biologically produced material does not occur, and thereby forming substantially dry particles each comprising a matrix formed of polymeric material and the biologically produced material dispersed substantially uniformly throughout the matrix, wherein the particles are beads having a size of from 30 microns to 2 mm, and
    separating the dried beads from the water immiscible liquid.

3. A process for making particles containing biologically produced material selected from the group consisting of enzymes, fungi, spores, bacteria, cells and antibiotics, in a matrix of polymeric material comprising:
    mixing film-forming polymeric material selected from the group consisting of water soluble polymers and oil-in-water emulsions of alkaline soluble polymers, the said polymeric material bring in an amount of at least 0. 5 times that of the biologically produced material on dry weight basis, with an aqueous liquor that is a fermentation broth concentrate containing the said biologically produced material and thereby forming an aqueous polymer phase throughout which the biologically produced material is substantially uniformly distributed,
    simultaneously or subsequently dispersing the said aqueous polymer phase in a water immiscible liquid in the presence of a dispersion stabilizer and thereby forming a substantially stable dispersion of the said aqueous polymer phase in the said water immiscible liquid, and
    azeotropically distilling the dispersion at a temperature that is below 70° C. and at which deactivation of the biologically produced material does not occur, and thereby forming substantially dry particles each comprising a matrix formed of polymeric material and the biologically produced material dispersed substantially uniformly throughout the matrix, the particles having a size of below 10 μm and being present as a stable dispersion of the particles in the water immiscible liquid.

4. A process according to claim 1 in which the biologically produced material comprises an enzyme suitable for use in detergents selected from the group consisting of amylase and lipase.

5. A process according to claim 1 in which the azeotroping is conducted at a temperature below 50° C.

6. A process according to claim 1 in which the dispersion stabiliser is an amphipathic polymeric stabiliser formed by polymerisation of hydrophilic monomer and hydrophobic monomer.

7. A process according to claim 1 in which the amount of polymeric material is at least 7 times the weight of the biologically produced material.

8. A process according to claim 7 in which the amount of the polymeric material is from 15 to 50 times the weight of the biologically produced material.

9. A process according to claim 1 in which the biologically produced materials an enzyme suitable for use in detergents and the polymer is selected from carboxymethyl cellulose and anionic synthetic polymers having a molecular weight of 4,000 to 300,000 and formed from ethylenically unsaturated carboxylic or sulphonic monomers and, optionally, non-ionic ethylenically unsaturated monomers.

10. A process according to claim 1 in which the polymer is formed from (meth) acrylic acid or a soluble salt thereof, optionally with acrylamide.

11. A process according to claim 1 in which the polymer is introduced as a salt of a polymer of an ethylenically unsaturated carboxylic acid monomer with a volatile amine, and the amine is at least partially evaporated during azeotroping in order to reduce the hydrophilic properties of the matrix.

12. A process according to claim 1 in which the polymer is introduced as an oil-in-water emulsion of a copolymer ethylenically unsaturated anionic monomer and water insoluble ethylenically unsaturated non-ionic monomer and in which the copolymer is soluble or swellable in alkali.

* * * * *